United States Patent
Dutta-Choudhury et al.

(10) Patent No.: US 6,289,492 B1
(45) Date of Patent: Sep. 11, 2001

(54) METHODS AND APPARATUSES FOR DEFINING A REGION ON AN ELONGATED OBJECT

(75) Inventors: Paul Dutta-Choudhury, Franklin; Len Picard, Newtonville; Yasunari Tosa, Arlington, all of MA (US)

(73) Assignee: Cognex Corporation, Natick, MA (US)

(*) Notice: Subject to any disclaimer, the term of this patent is extended or adjusted under 35 U.S.C. 154(b) by 0 days.

(21) Appl. No.: 09/303,214

(22) Filed: Apr. 30, 1999

Related U.S. Application Data

(60) Provisional application No. 60/112,906, filed on Dec. 18, 1998.

(51) Int. Cl.⁷ .................................................. G06F 17/50
(52) U.S. Cl. ............................................................ 716/5
(58) Field of Search ...................................... 716/1, 5, 19

(56) References Cited

U.S. PATENT DOCUMENTS

| | | | |
|---|---|---|---|
| 4,163,212 | * 7/1979 | Buerger et al. | 716/19 |
| 4,864,514 | * 9/1989 | Yamanaka et al. | 716/19 |
| 5,119,436 | 6/1992 | Holdgrafer | 382/8 |
| 5,125,036 | 6/1992 | Raghavan et al. | 382/8 |
| 5,581,632 | 12/1996 | Koljonen et al. | 382/150 |

OTHER PUBLICATIONS

Cognex 3000/4000/5000, Vision Tools, Rev 7.4, Chapter 4, pp. 208–231 (1996).

* cited by examiner

*Primary Examiner*—Trong Phan
(74) *Attorney, Agent, or Firm*—Tracy Calabresi; Russ Weinzimmer

(57) ABSTRACT

Methods and apparatuses are disclosed for defining a locus of viable points on an elongated object, such as a locus of viable bond points on a lead of a lead frame. The locus guides the bond point positioning of a wire bonder so that the number of unacceptable wire bonds is reduced. The locus is a region adapted to receive a bond, and is defined such that for any bond centered therein, the probability of forming an unacceptable bond is reduced by offsetting the locus from at least a portion of the lead edge(s) by a minimum-offset distance. The minimum-offset distance is based on various factor(s), such as user tolerance and bond width. Further, the definition of the locus is independent of lead shape, and consequently works with a variety of lead shapes. The locus can also have various shapes for a single lead, and the shapes can vary depending on the application. The method and apparatus herein disclosed describe a variety of methods to detect the leads and define the size, position, and shape of the locus during training. Preferably, the lead tip is also detected so that the locus can be defined based on an offset from the front of the lead. During operation, characteristics of the locus and/or the target bond point are used to relocate the lead and refine the target bond/point before bonding. Alternative embodiments disclosed include inspecting the leads.

41 Claims, 13 Drawing Sheets

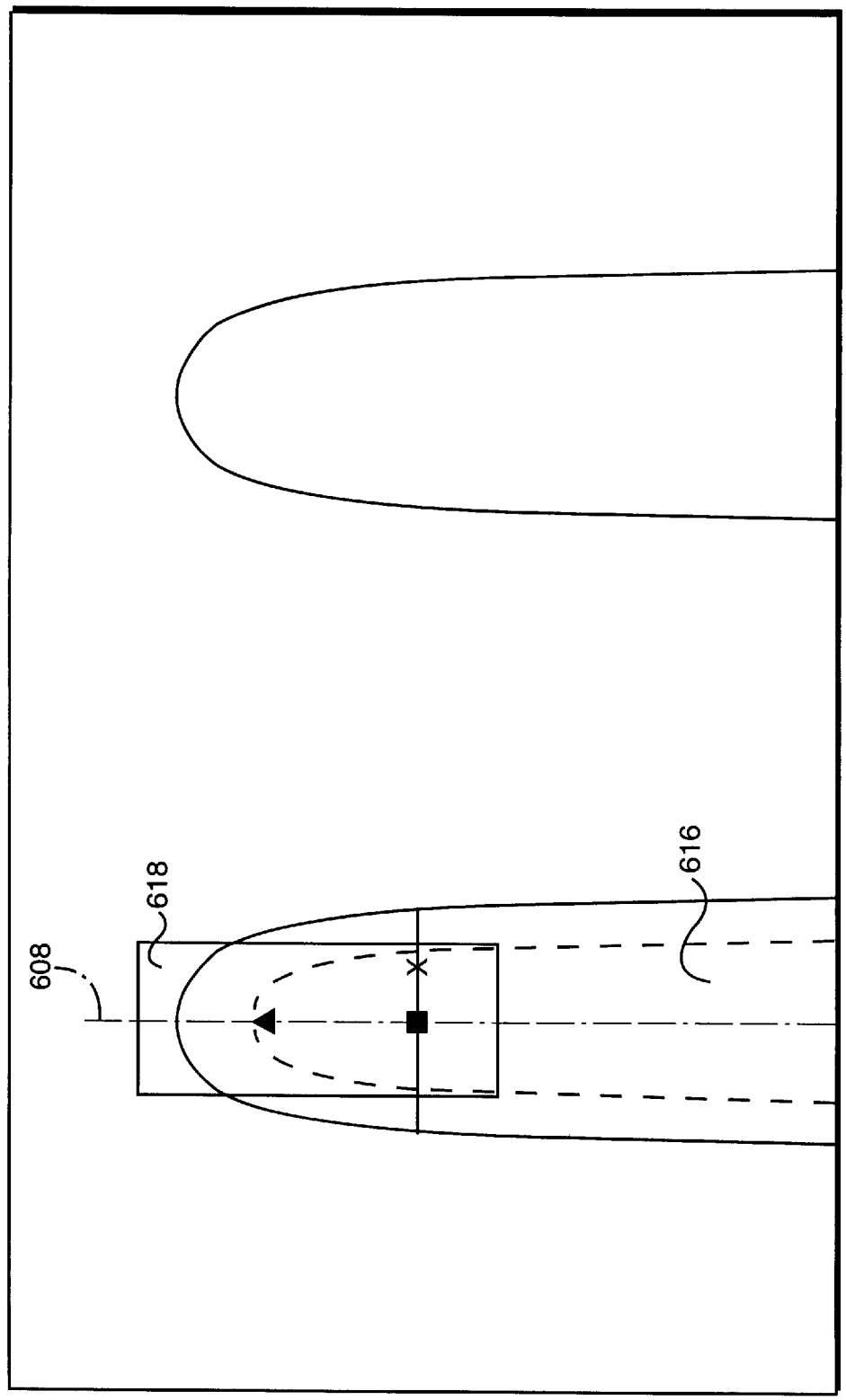

METHODS AND APPARATUSES FOR DEFINING A REGION ON AN ELONGATED OBJECT

This application claims the benefit of U.S. Provisional Application No. 60/112,906, filed Dec. 18, 1998.

FIELD

This invention relates to machine vision systems, and particularly to machine visions systems for use with semiconductor chip wire bonding devices, and similar bonding devices.

BACKGROUND

Semiconductor devices, such as integrated circuit chips, are electrically connected to leads on a lead frame by a process known as wire bonding. The wire bonding operation involves placing and connecting a wire to electrically connect a pad residing on a die (semiconductor chip) to a lead in a lead frame. Once all the pads and leads on the chip and the lead frame have been wire bonded, it can be packaged, often in ceramic or plastic, to form an integrated circuit device. In a typical application, a die or chip may have hundreds of pads and leads that need to be connected.

As circuit density of integrated circuit chips has increased, the configuration of the lead frames, which provide input and output to the chips, has also become increasingly complex. The leads to which wire bonds must be made have become increasingly smaller, more varied in shape, and more numerous and, therefore, more difficult to form wire bonds thereto.

Before bonding, the wire bonder system learns the expected positions and orientations of the die, the lead frame, the pads, and the leads. Typically, the location and orientation of the die are indicated with respect to two reference points, such as fiducials. The wire bonder learns the pad shape and the pad locations on the die. Similarly, the location of the lead frame is indicated by one or more reference points, and the wire bonder learns the lead positions with respect to the lead frame.

The position of the target bond points on the leads is determined in a number of ways. In one technique, operators manually place a location of a target bond point on each lead to train the location of the leads and the target bond points to the system. In another technique, such as that described in U.S. Pat. No. 5,119,436, (the '436 patent) a manually trained location of a target bond point is refined by the pattern recognition systems of the wire bonder. The system then automatically determines a location of target bond points on successive leads.

The wire bonder uses the trained data, during operation, to bond the wires. Before bonding, typically, the system relocates the leads. However, for various reasons, some of the bonds formed are unacceptable.

Unacceptable bonds include, for example, missed bonds, misshapen bonds, or partial bonds. A missed bond is positioned off the lead and fails to form the electrical connection required for proper operation of the chip. A partial bond passes electrical testing during quality inspection, but will typically fail in the field.

Among other reasons, unacceptable bonds occur because of improper placement of the target bond position along the normal axis of the leads. For instance, the trained target bond position can be too far to the side of a lead. Further, when the training information about target bond points is applied to subsequent parts, the variation among the parts can cause unacceptable bonds, particularly if a trained bond position was offset from the center of the lead.

Among other reasons, unacceptable bonds also occur because of errors in lead detection. Lead detection errors can occur because of non-robust techniques, such as the one-dimensional scanning of intensities employed in the '436 patent, cited above, poor image quality, or a combination of both. Poor image quality is caused by poor lighting, poor focusing, specular reflections off the leads and the background of the image, noise, and irregularities in the surface of the leads, among other causes, as is known in the art.

A further reason for unacceptable bonds is the failure or inaccurate resolution of the target bond position along the length of the leads. The manual method does not resolve the target bond position along the length of the leads. Although the manual method is reasonably accurate and robust for large leads with parallel sides, typically its failure rate is high for smaller leads and leads with non-parallel sides. The '436 patent does resolve the target bond position along the length of the leads for parallel leads. The lack of robustness of the '436 patent, either alone or combined with poor image quality, however, leaves unclear the effect of the length resolution on the number of unacceptable bonds.

Further, the '436 patent does not address non-parallel leads.

SUMMARY

The invention provides methods and apparatuses for defining one or more positions on elongated objects. In one embodiment, data is acquired that represents the elongated objects, where the data is used to determine at least a portion of the edges of the elongated objects. The edges are then used to define a locus of viable points on each of the elongated objects, where the locus is positioned offset from a portion of at least one edge by at least a minimum-offset distance. The locus has a longitudinal axis and optionally a reference position.

In a preferred embodiment, the locus defines the location for one or more target bond points on selected leads (elongated objects) of a lead frame. The longitudinal axis of the locus is the bisector of the lead.

The locus is a region on the leads that decreases the likelihood of the formation of unacceptable bonds of wires to the leads of the lead frame. Among other aspects, the invention recognizes that the likelihood of an unacceptable bond is decreased when a target bond position is offset from at least a portion of the lead edges by at least a minimum-offset distance. Thus, the bond will more likely be on the lead, and not be partially on the lead, or miss the lead entirely. In a preferred embodiment, the locus is offset from all lead edges except the base, that is, offset from the lead sides and the lead "tip".

The minimum-offset distance can vary along edges of the lead. In one embodiment, the minimum-offset distance is equal to at least one-half the dimension of the bond. Using this dimension to define the locus, a bond centered at a target bond position within the locus is more likely fully on the lead because the bond is not large enough to reach a lead edge.

In a preferred embodiment, a "tip" of each of the selected leads is also detected to refine the definition of the locus to be a region between the sides that is offset from both the sides and the "tip" by at least a minimum-offset distance.

In one embodiment, the "tip" is defined as the intersection of a bisector and a portion of one edge of each of the leads, where the bisector is a line that is substantially equidistant between the sides of each lead near the "tip". More particularly, the bisector is a line substantially equidistant between the lines that represent part of the lead sides. This definition of "tip" for a lead is substantially independent of the shape of the lead. Therefore, the definition can be used with leads having varied shaped sides, such as leads with one or more curved sides, tapered sides, or straight sides, whether the lead sides are parallel, converging, diverging or angled, where angled leads have an angled bisector comprised of more than one line, for example.

In an alternate embodiment, the "tip" is defined as a center point where a line normal to the bisector first touches the lead when moved toward the "tip" from a position outside of each lead. This definition can also be used with any shaped lead.

In a preferred embodiment, the method of the invention is divided into two parts being: training and run-time. The loci are defined for leads of a training device. Thereafter, the loci are used to position the target bond point on the leads of a run-time device. In this embodiment, the leads of the training device and the leads of the run-time device correspond one-to-one, and the training device is an instance of the run-time device or a model to be used with a plurality of run-time devices.

In one embodiment, at least a portion of each side of the run-time leads is detected by searching an image of the run-time leads. Once the run-time leads are located, the loci of the corresponding training leads are used to position one or more bond points on the run-time leads.

Alternatively, the run-time leads are searched at a position directed by the loci of the corresponding training leads. More particularly, a first window, which defines the portion of the run-time lead and background to search, is aligned using the locus of the corresponding training lead. The first window is aligned substantially normal to the longitudinal axis of the locus and aligned with the optional reference position of the locus, such as centered on a target bond position. The image within the window is searched for at least a portion of each side of the run-time leads. Thereafter, one or more bond points on the run-time leads are positioned between the sides. Preferably, the one or more bond points are within the locus of viable bond points.

In further aspects of the invention, a wire is bonded at or near the target bond point(s) on selected leads of the lead frame.

In a preferred embodiment, lines, as opposed to part of an edge, are used to detect portions of the lead sides during training and/or run-time. The locus is defined as an offset from the lines by the minimum-offset distance.

One of the advantages of the invention, among others, is that the locus defines one or more viable positions upon which the bonds can be placed instead of a single viable bond position.

Further, defining the locus after resolving the longitudinal axis of the leads enhances target bond position placement.

Furthermore, the definition of loci and "tip" can be used across varied shaped leads, allowing a part having more than one shaped lead to be processed without interruption, and allowing multiple parts to be processed using the same method.

The invention solves some of the problems of the prior art, including, for example, enhancing reliability of the position of target bond points during training, robustly locating target bond positions in images, resolving the target bond position along both the normal axis and the longitudinal axis of the leads, and accommodating non-parallel leads.

In further aspects, the invention provides an apparatus in accord with the methods described above. The aforementioned and other aspects and objects of the invention are evident in the drawings and in the description that follows.

BRIEF DESCRIPTION OF THE DRAWINGS

The invention will be more fully understood from the following detailed description, in conjunction with the accompanying figures, wherein:

FIGS. 6A and 6B illustrate two embodiments of the invention for locating target bond positions;

DETAILED DESCRIPTION OF THE DRAWINGS

The methods and apparatuses define a locus of viable points on a plurality of elongated objects. The method is particularly useful for defining a locus of viable bond points on leads of a lead frame. Though this is the form of a preferred embodiment, this embodiment should be considered illustrative, and not restrictive.

Figure 1:
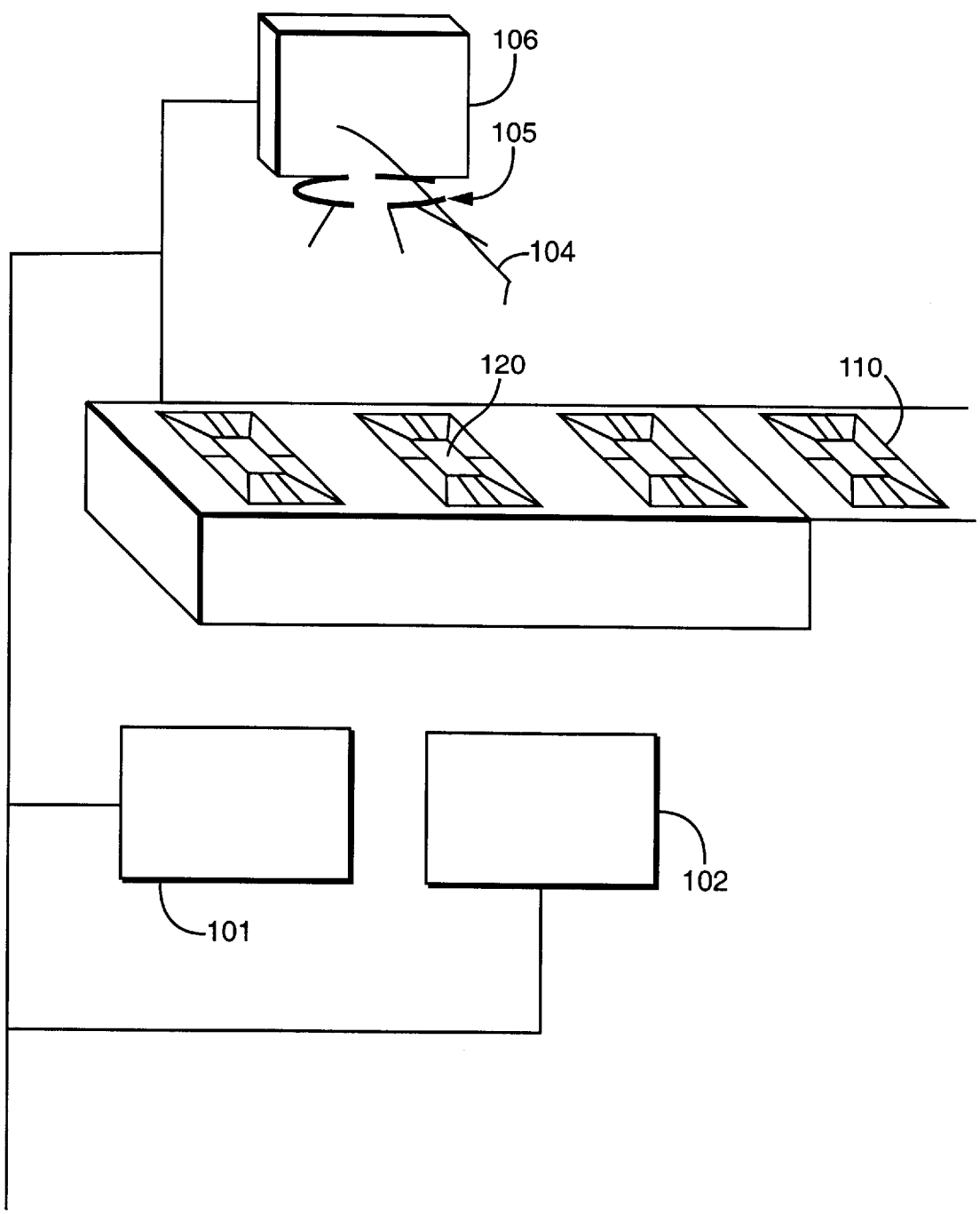
FIG. 1 is a schematic drawing of a wire-bonding system according to the method and apparatus of the present invention.
Figure 2:
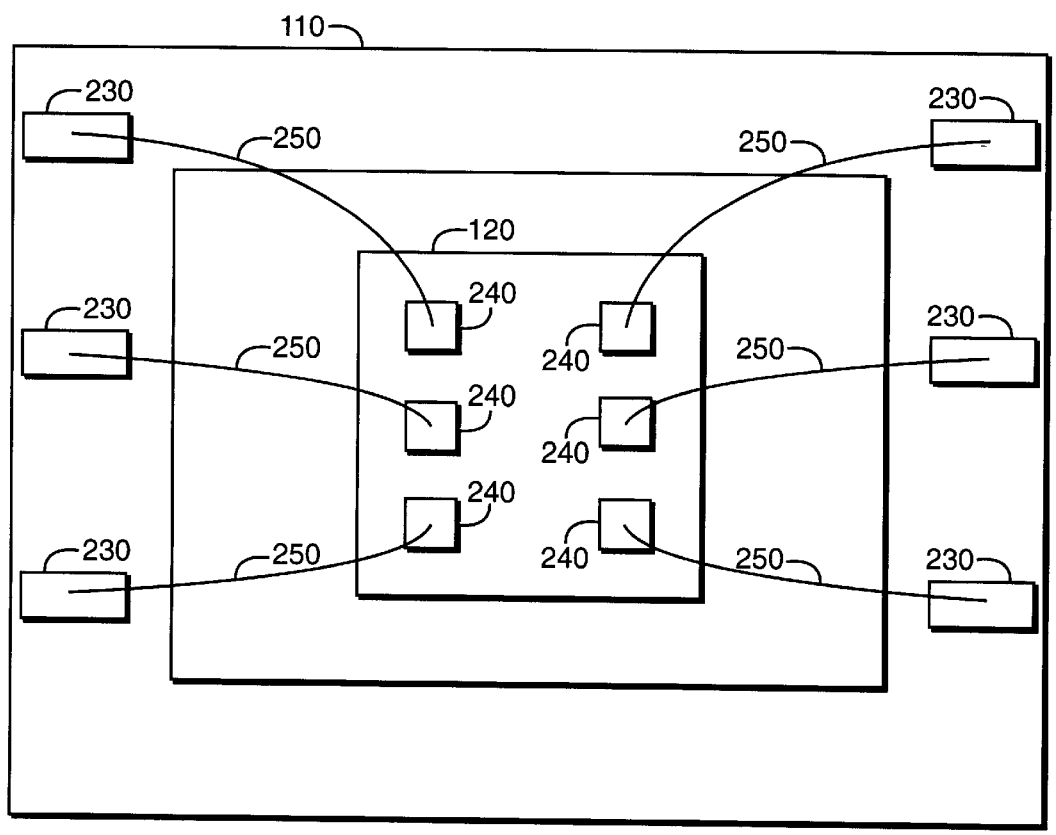
FIG. 2 is a schematic top view of a semiconductor chip with wires bonded to leads.

Turning to FIG. 1, a typical wire-bonding system according to the methods and apparatuses of the present invention is shown. In this system, semiconductor chips 120, on lead frames 110, are bonded by a bond head mechanism 104, which is coupled to a host controller 101. The host controller 101 is also coupled to an image processor 102, which is in communication with a video camera 106. Light 105 provides illumination. FIG. 2 shows a top view of one of the semiconductor chips 120 in which pads 240 are bonded by wires 250 to leads 230 on the lead frame 110.

In a preferred embodiment, the image processor 102 is implemented on a conventional digital data processing system. Those skilled in the art will appreciate that the image processor 102 may be implemented on a special purpose device constructed in accordance with the teachings herein.

The image processor 102 executes the procedures described hereinbelow, and it comprises, at least, a defining device and a detecting device. The defining device is adapted to receive data on the leads and define a locus of viable bond positions on the leads (target bond positions). The detecting device is adapted to locate features of the leads, such as edges and/or lines of the sides and/or tips. In one embodiment, the detecting device locates edges of the sides in a training image and/or a run-time image. Once the leads are located, one embodiment inspects the leads for compliance with specifications. A preferred embodiment positions a target bond point between sides of the leads.

Figure 3A:
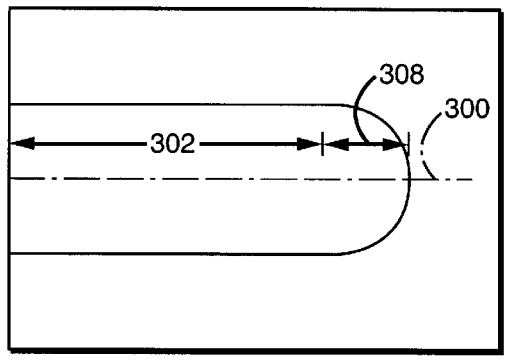
FIGS. 3A–3E illustrate an instance of each leads locus of viable bond positions.

The one or more target bond points are positioned to decrease the likelihood of the formation of an unacceptable bond on the leads. Partial or missed bonds are minimized by a bond point that is maximally separated from the leads edges, and, therefore, is preferred. A maximally separated bond point is centered along a subset 302 of the lead bisector 300, an example of which is shown in FIG. 3A, not drawn to scale. Typically, the offset from the lead base (not shown) is not considered because bonds are formed far enough from the lead base. Accordingly, as used herein, the edge(s) or portion of the edge(s) corresponding to the lead base is not part of the definition of the locus.

Figure 3D:
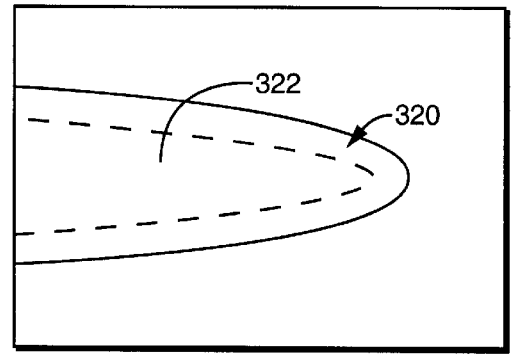
Figure 3B:
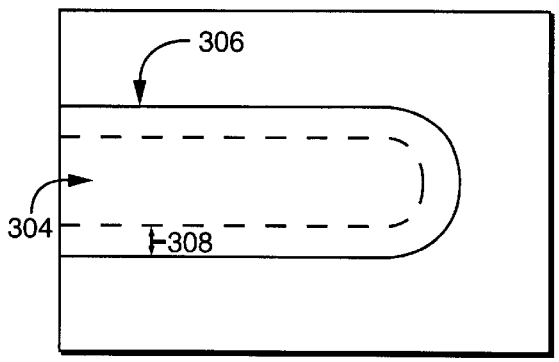

The invention further recognizes that the likelihood of the formation of an unacceptable bond is sufficiently minimized by positioning a target bond point within a locus of viable bond positions 304, where the locus of bond positions 304 is offset from at least a portion of the lead edges 306 by at least a minimum-offset distance 308, as illustrated in FIG. 3B, not drawn to scale.

The minimum-offset distance 308 ensures that a bond made at one of the bond points within the locus will not form a partial or missed bond. The minimum-offset distance is large enough to ensure that once a bond point within the locus receives a bond, parts of the bond will not, or substantially will not touch, or go over the edges.

The minimum-offset distance is based on the application and can accommodate one or a number of factors, including bond shape and tolerances input by a user, for example.

Figure 4B:
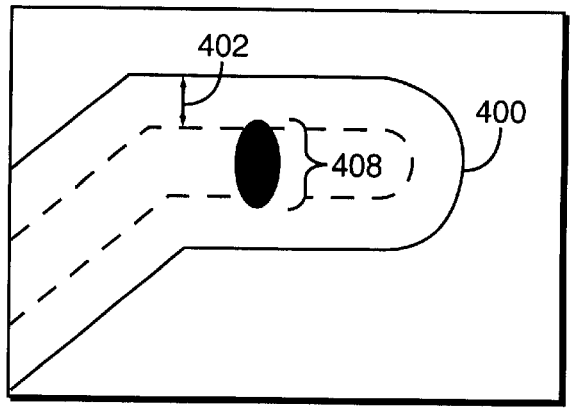
FIGS. 4A–4C illustrate the same lead and varying instances of the locus of viable bond positions for the same lead.
Figure 4A:
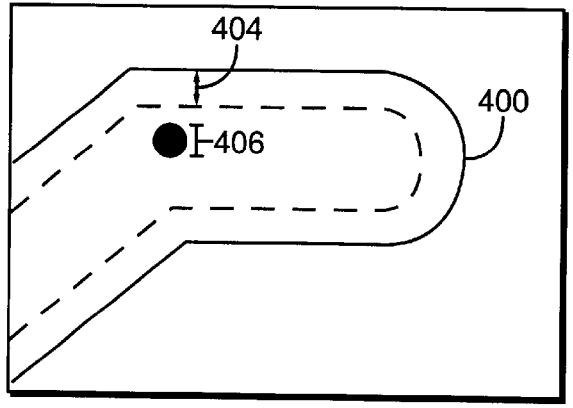
Figure 4C:
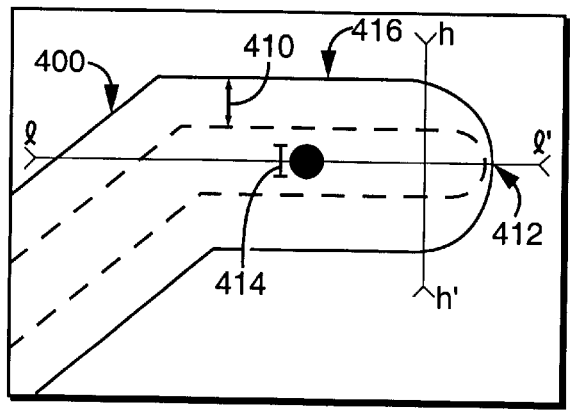

The bond shape affects the minimum-offset distance as illustrated in FIGS. 4A–4C, which show the same lead having varying instances of the locus of viable bond positions, not drawn to scale. The minimum-offset distance 404 is small when the width of a bond 406 is small relative to the width of the lead. In contrast, for the same lead 400, the minimum-offset distance 402 is larger when width of the bond 408 is larger.

The shape of the bond, not just the width, affects the minimum-offset distance and, thus, the shape of the locus. As shown in FIG. 4C, the minimum-offset difference 410 can vary along the lead 400. For a crescent-shaped bond 414, the minimum-offset distance 410 is larger around the lead sides 416 than near the lead tip 412 because a crescent-shaped bond 414 has a smaller dimension along the lead longitudinal axis, 1–1', than along the normal axis, h–h'. It will be apparent to those skilled in the art that the minimum-offset distance does not need to be constant and can vary along each side and/or near the tip.

The user can change the minimum-offset distance depending on the positional uncertainty of the wire bonder, the application, and/or the objectives of the user. Further, the wire bonder could be taught the bond shape during training and, thereafter, automatically calculate the minimum-offset distance for each lead. A value greater then the minimum-offset distance is used to be more conservative.

Figure 3E:
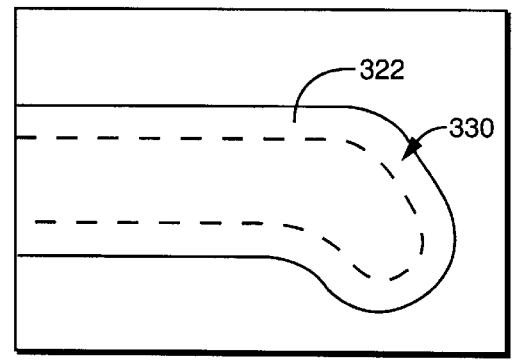
Figure 3C:
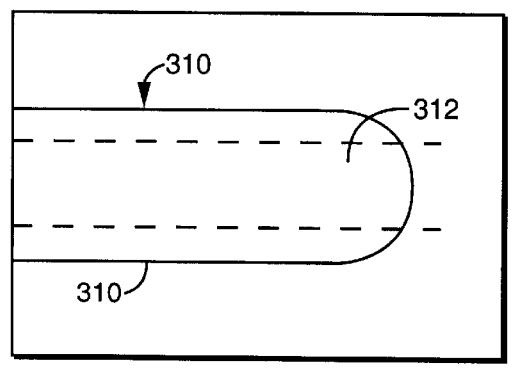

A less ideal embodiment of the locus is illustrated in FIG. 3C, not drawn to scale, which shows a lead having a locus of viable bond points 312 offset only from the lead sides 310. This is not a preferred locus 312 or a minimum-offset distance for any lead because bond positions formed at, or near, the tip within the locus 312 may produce unacceptable bonds. However, in some applications, the locus 312 is sufficient.

FIGS. 3D and 3E illustrate two other examples of leads 320 and 330 and one instance of a preferred instance of their loci 322 and 332, respectively. One skilled in the art should appreciate that the definition of the locus of viable bond points is adaptable to other lead shapes.

Figure 5:
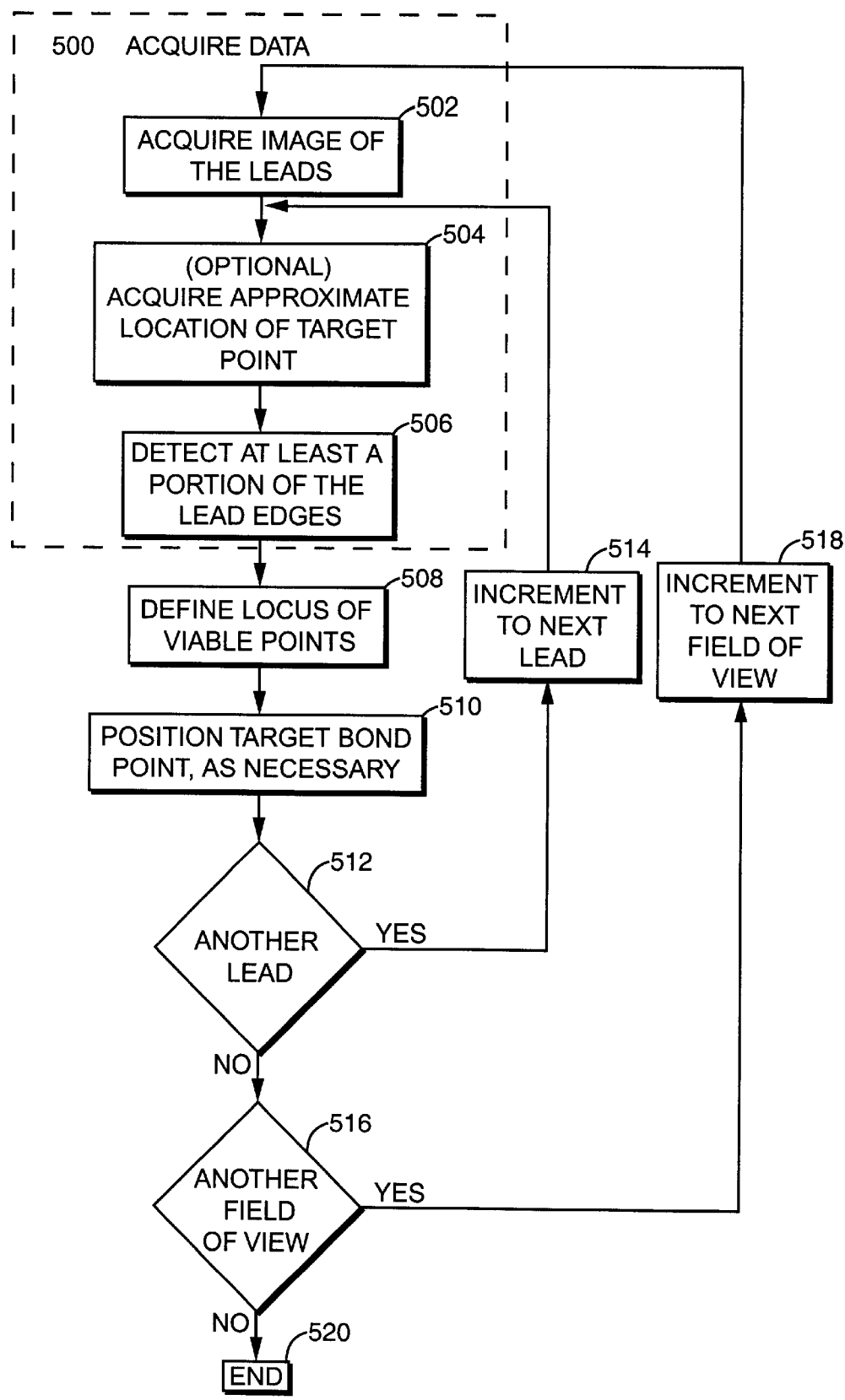
FIG. 5 is a flowchart of embodiments of the method of the invention.

Turning to FIG. 5, FIG. 5 is a flowchart of one embodiment of the method of the invention for defining a locus of viable bond points on leads, where the steps of the method are denoted in the detailed description in parentheses. In a preferred embodiment, steps (500)–(520) constitute the training portion of the method.

The first step of training is to gain an approximate location of at least part of the edges of the leads and optionally a target bond position (500).

The approximate location of said edges and the optional target bond point could be found by acquiring data files from package specifications. Similarly, the data can be synthesized from a geometric description of the leads combined with any information required to calibrate the geometric description of the leads to pixel size(s) and aspect ratio(s) of the camera imaging system that is used to acquire the test image.

Preferably, however, the training data is acquired by acquiring an image of the leads (502), and detecting at least a portion of the lead edges (506).

The entire device or part of the device can be imaged at one time. If the image contains less than the entire part, steps (502)–(514) are repeated on the next field of view (516).

Within the field of view, the sides of the leads can be found by searching the field of view (506) using the an application of the Hough Transform, as hereinafter described, or by using techniques, such as boundary tracking and connectivity analysis, for example. The search is conducted over the field of view or at the location given by a geometric description, the center of mass lines that comprise the sides of the leads, or other methods that should be evident to those skilled in the art.

Preferably, however, only a sub-region of each field of view is searched for the lead edges. The sub-region is defined by a window, such as window 602 shown in FIG. 6A, which illustrates leads 600 within a field of view 610, not drawn to scale. Window 602 has an origin, typically defined in the upper-right hand corner of the window.

Figure 6A:
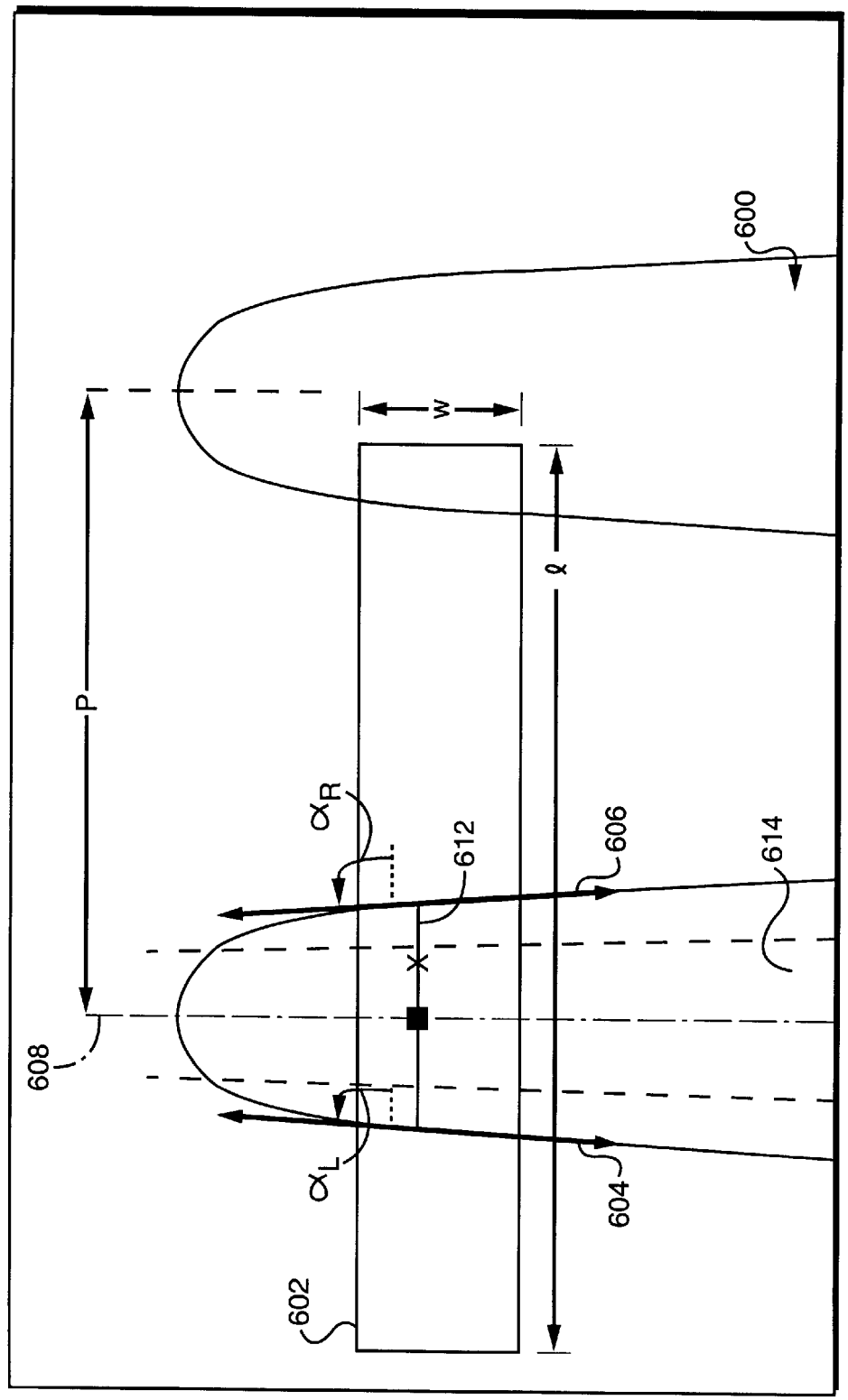

The sub-regions are focused upon by the machine vision system using the optional target bond point (504). FIGS. 6A and 6B illustrate target bond points designated "X". An operator can provide the approximate location of the target bond point or it can be given by other methods, including, searching the field of view using a model of the lead tip with a pattern recognition search tools, such as the SEARCH TOOL, an application of normalized correlation search sold by Cognex Corporation, for example. The approximate location of the target bond point is provided relative to the lead frame, the image coordinate system, or a user-supplied coordinate system. The location is given as coordinates of the point, parameters of a window having the target bond point at the center, or by other representations known in the art.

Instead of acquiring the optional target bond point for each lead, a single optional target bond point can be acquired and the locations of subsequent optional target bond points are extrapolated therefrom. The subsequent optional target bond points can be in the same or prior field of view, provided the appropriate calibration data between fields of view is provided, as necessary.

In this embodiment, said edges are detected by processing the sub-region of the image within the window 602. The length, l, of the window is long enough so the region includes the lead sides. The region of interest within the window 602 can be searched by scanning a one-pixel wide window 602 for the intensity of the pixels along l and evaluating the changes in intensities between neighboring pixels for an edge. Alternatively, a region of interest within a two-dimensional window 602 can be summed along the width, w, into a one-dimensional projected intensity image and evaluated, as known in the art, or using the Cognex CALIPER TOOL, an application of an edge detection tool sold by Cognex Corporation further described in Vision Tools, Chapter 4, CALIPER TOOL, Cognex Corporation Revision 7.4, 1996, pp. 208–31, incorporated herein by reference.

The invention recognizes that one-dimensional scans and projections in real conditions often do not generate reliable lead side position information. Primarily, the lighting, the nature of the leads, and the background create edges that are easily confused with, if not indistinguishable from, edges associated with sides of the leads, and thus, produce erroneous lead side position information. A better lighting system for leads or by other accommodations know in the art can minimize the extraneous edge information. However, systems are often tailored to image elements other than leads, leaving a poor quality image of the leads. Accordingly, the invention recognizes that more reliable lead information is generated when the field of view and/or sub-region within the window is processed using an algorithm that preserves the two-dimensional nature of information, such as a Hough Transformation, as known in the art, or preferably, the methods and apparatuses described in co-pending provisional patent application of Paul Dutta-Choudhury, Len Picard entitled "Method And Apparatus For Refining Groupings Of Data From An Image", incorporated herein by reference, filed concurrently herewith, and assigned to Cognex Corporation, for example.

The Hough transformation generates line characteristics, such as angle, $\alpha$, and normal distance, d, from the edge information, where the angle is measured relative to the x-axis of an image coordinate system or a user coordinate system as being positive counterclockwise from the x-axis to the line.

Each line that represents a lead side 604 and 606 is parameterized by the Hough Transformation and represented by $[\alpha_L, d_L]$ and $[\alpha_R, d_R]$, respectively. When more than one line is generated, one or more constraints are applied to rank the lines to determine which represents the lead sides. Constraint techniques are known in the art. For instance, lines having the proper polarity and straddling the target bond point are ranked higher.

Figure 7A:
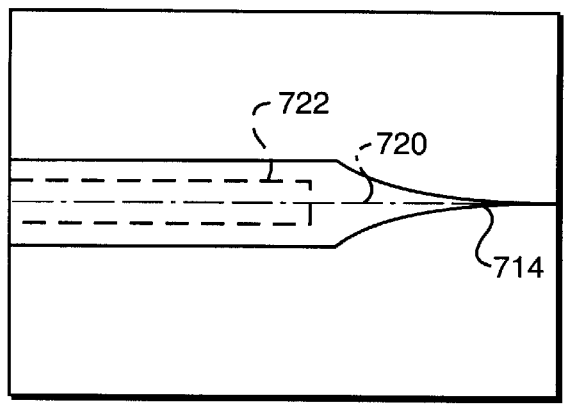
FIGS. 7A–7C illustrate three leads having different lead tip shapes.
Figure 7B:
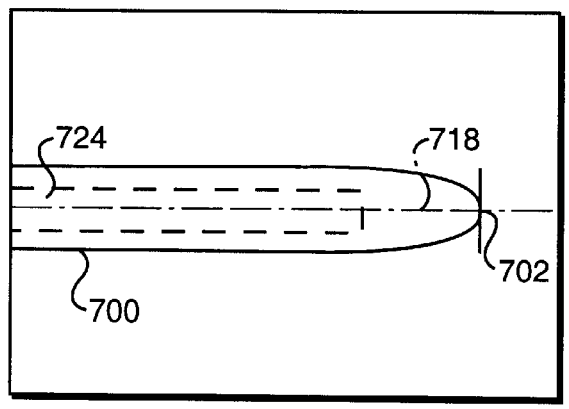
Figure 7C:
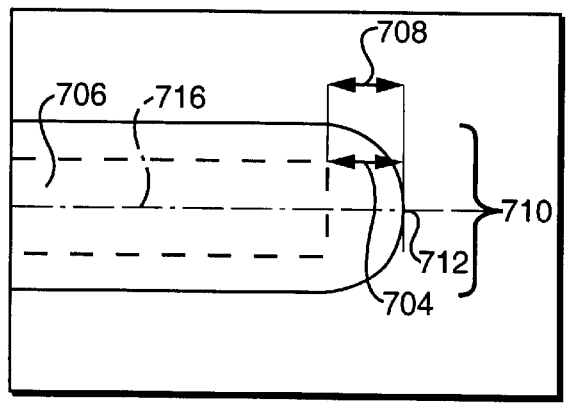

When the locus of bond positions extends over the "tip" of the lead, such as locus 614, only the sides of the leads need to be detected during training. However, to define a preferred locus that is offset from the "tip" as well as the sides, such as locus 616, 722, 724, and 726, at least one point on the front of the lead also needs to be located. FIGS. 7A–7C illustrate three leads having different lead tip shapes, not drawn to scale.

In one embodiment, a locus 616 defined with edge tracking techniques is preferred, where the minimum-offset distance is calculated on an edge point-per-point basis.

In some applications, it is sufficient and preferred to define one point as the tip and use a minimum-offset distance from that point across the front of the lead, such that a terminating end of the locus is flat, such as loci 722, 724, and 706.

The tip can be defined numerous ways, such as the farthest point from the base (not shown), for example. What constitutes the tip 702 of the parallel lead 700 with a symmetrical tip is evident. However, for many other leads, what constitutes the "tip" is less obvious and not always appropriate for the definition of the locus.

The tip can be defined as the furthest point on the lead, such as point 704. Arbitrarily, if the defined "tip" is a line instead of a point, any point along the line can be used as the tip, such as the mid-point, or center of mass, for example. The locus 706 is then defined as offset across the front of the lead 710 a minimum-offset distance 708 from point 704. The locus 706, however, does not guarantee that all points on the front of the lead 710 are at least the minimum-offset distance 708 from the edge. Thus, the locus 706 does not fully satisfy the efforts to minimize formation of unacceptable bonds.

Alternately, the tip is defined as the point 714, 702, and 712, where a bisector, such as 718, 720, and 716, crosses the front of the lead. This definition of a tip is applicable to any shaped lead, where only the bisector closest to the tip is used. This definition of tip, however, also does not guarantee that a point a minimum-offset distance from the tip is substantially the same distance from all points comprising the front of the lead.

Despite the shortcomings, both definitions of "tip" produce consistent results for leads with similar tips, regardless of the shape of the lead sides. The shape of the front of the lead, and, therefore the definition of the lead "tip" chosen will vary depending upon the application in light of the teachings herein.

Returning to FIG. 6, with continuing reference to FIG. 5, several methods known in the art will find the front of the lead within a field of view or sub-region of the image, such as statistical analysis and edge tracking on all or part of the lead, for example. In a preferred embodiment, the front of the lead is found by searching a sub-region within a window 618, which is positioned orthogonal to the window 602. Depending on the shape of the front of the lead, one method may be preferable over another. The position of each "tip" can be resolved, a single "tip" can be located and the positions of subsequent tips extrapolated therefrom, or subsequent tips can be located using methods known in the art. The subsequent tips can be in the same or prior field of view provided the appropriate calibration data between fields of view is known, as necessary.

Once a portion of the edges and/or lines of the lead sides and/or front are located (506), the boundaries of the locus are defined (508) as a translation from the edges and/or lines inward by at least the minimum-offset distance. The locus has a longitudinal axis that is the same as a bisector of the lead, where the bisector is described hereinafter.

Once the locus is defined, the target bond position is provided or adjusted, if necessary (510). In one embodiment, if the target bond point is within the locus, the training for that lead is completed. In a preferred embodiment, even if the target bond point is within the locus the position of the target bond point is adjusted to be more centered on the lead.

Returning to FIG. 6A, preferably, the target bond point is positioned by computing a lead bisector 608 and adjusting the target bond point from X to a position "■" which is the midpoint of a line 612 normal to the bisector 608 that includes the target bond point X. The parameters [$\alpha_B$, $d_B$] of the lead bisector 608 are derived using the lines 604 and 606 of the lead sides, parameterized by [$\alpha_L$, $d_L$] and [$\alpha_R$, $d_R$], respectively, and known mathematical concepts. The parameters are given by:

$$\alpha_B = \frac{\alpha_R + \alpha_L}{2}$$

$$d_B = \frac{d_R + d_L}{2\cos\left(\frac{\alpha_{RN} - \alpha_{LN}}{2}\right)}$$

Where $\alpha_{RN}$=the angle of the line normal to the line representing the right side of the lead and Where $\alpha_{LN}$=the angle of the line normal to the line representing the left side of the lead.

Other variations of the above may also be used to find the lead bisector without deviating from the scope of the invention.

Preferably, the target bond point is resolved, not only in the transverse direction, but also along the longitudinal length of the lead for uniformity purposes, cost, among other reasons. Wire is often manufactured of costly materials, such as gold. Accordingly, the invention recognizes that to preserve wire, the preferred position of the target bond point is as close to the tip as possible while the position still sufficiently minimizes the possibility of forming an unacceptable bond (being within the locus). Therefore, the target bond point is moved (510) along the bisector 608 towards the tip, from ■ to ▲, while remaining within the locus 616.

It should be apparent that, the target bond point can be adjusted using other methods, such as computing the center of mass of the lead, where the lead is all pixels within the edges; this would work for symmetric leads.

If there is another lead within the field of view (512), the operation is repeated until there are no more leads within the field of view (514). The target bond point of the next lead within the field of view is given or measured from the pitch, p, of the leads, determined during training, and from the position of the previous target bond point. The pitch is the distance between the centers of the lead, as known in the art.

If each field of view only contained part of the leads to be trained (516), the next field of view is addressed (518) and the steps (500)–(516) are repeated until there are no more leads left to train, then the training ceases (520).

Alternatively, the bond could be formed on the lead before training the next lead. In most wire bonder apparatuses, however, this is an inefficient implementation as the wire bonding head and the camera head are typically placed on the same attachment and need to move between bond point positioning and bonding, as is known in the art.

Also, as known in the art, training for one type of device can be conducted once and saved for future use.

Further, as known in the art, only selected leads need to be bonded for various applications. Therefore, only those leads need to be trained.

Figure 8A:
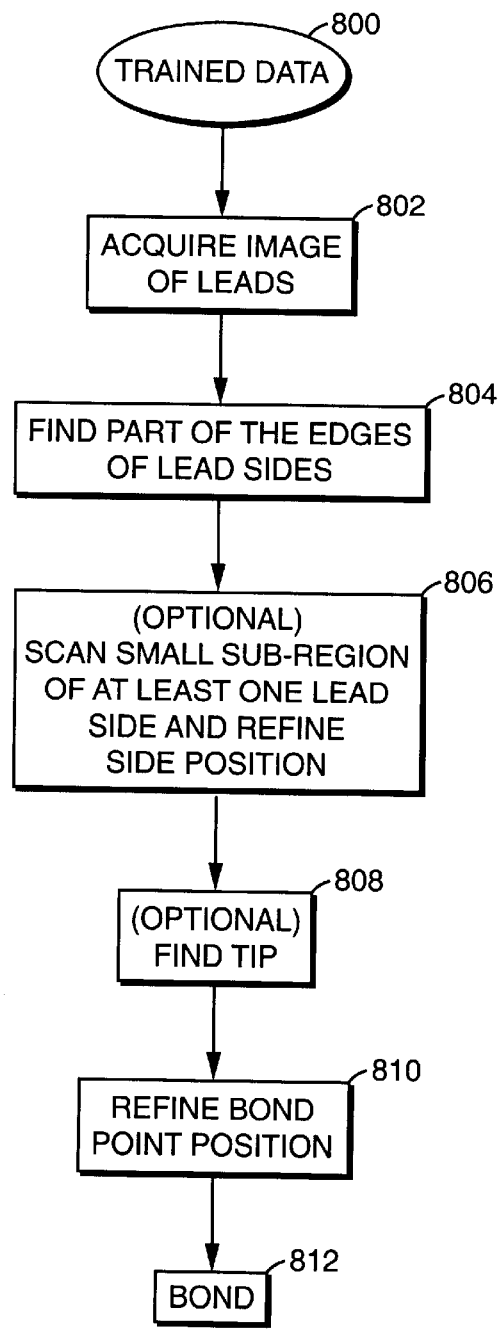
FIGS. 8A and 8B are flowcharts of embodiments of a run-time portion of the method of the invention.
Figure 8B:
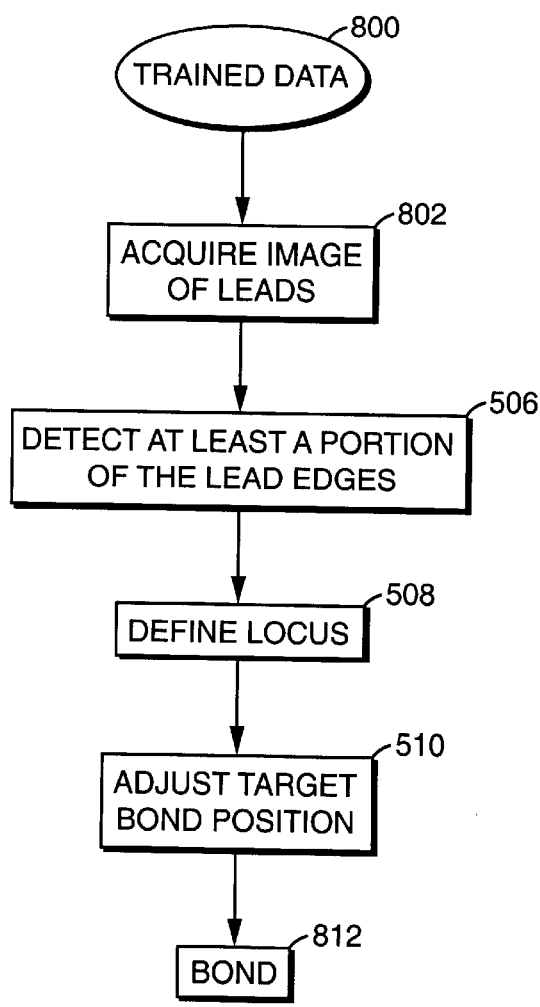

Turning to FIGS. 8A and 8B, the FIGS. illustrate two alternative embodiments for run-time in the method of the invention, where the steps of the method are denoted in the detailed description in parentheses, where like numerals indicate like steps. The run-time portion of this embodiment receives the trained data (800), which includes, at least, the target bond position, the angle of the longitudinal axis of the locus, the tolerances desired by the user, and optionally the location of the tip. When the target bond position is not readjusted along the longitudinal axis of the lead during run-time, the training position of the tip is not needed. Therefore, the position of the tip is optionally included in the trained data.

The leads are imaged (802) and relocated within the image before bonding by detecting at least a portion of the lead sides (804). A less time intensive technique of detecting the sides is preferred over the line finder technique previously described.

Further, it is preferred a sub-region of the field of view is searched, although the entire field of view can also be searched.

As hereinbefore described, the intensities within a two-dimensional window are summed along one axis and evaluated. The process is illustrated with reference to FIGS. 9–9B.

Figure 9:
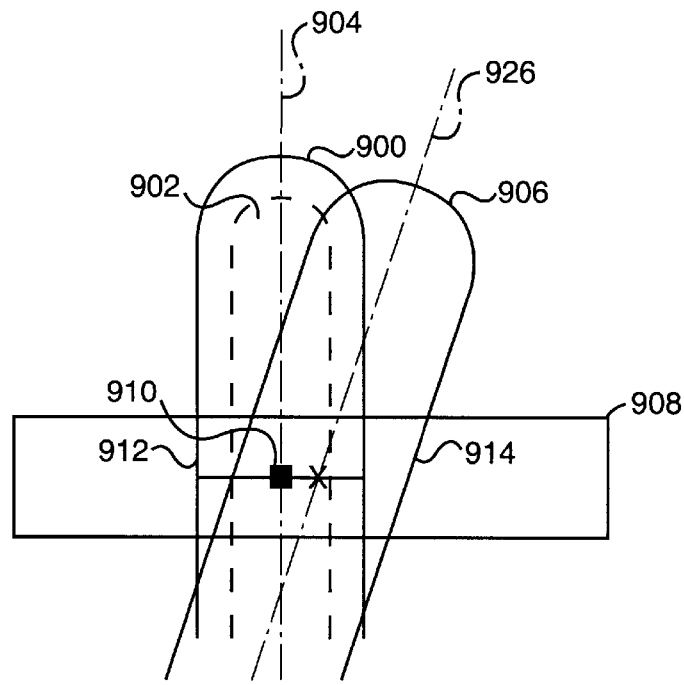
FIGS. 9–9B illustrate part of a lead at a training and a run-time position, a graph a one-dimensional intensity image of the width of the lead, and a first derivative of the graph, respectively.
Figure 9A:
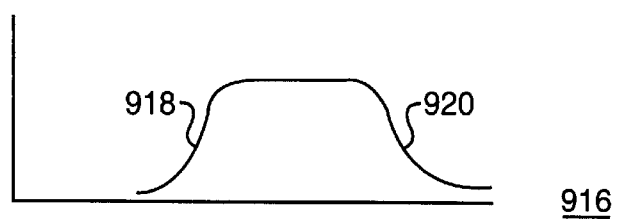
Figure 9B:
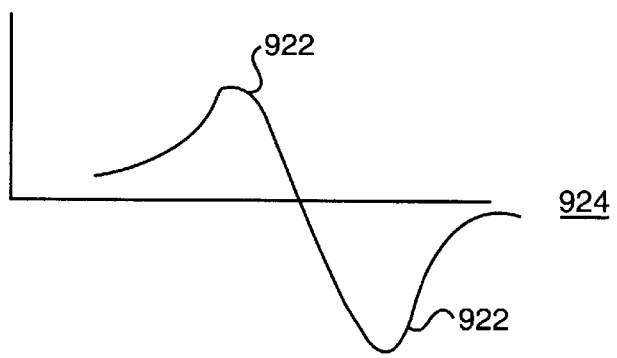

FIG. 9 illustrates a position of a trained lead 900, locus 902, and longitudinal axis of the locus 904 superimposed over a run-time image of a lead 906, a bisector of the lead 926, and a search window 908. The elements are not drawn to scale and exaggerated for illustration purposes. The window 908 is aligned substantially normal to the longitudinal axis 904 of the locus 902 and it encloses the target bond position 910 determined during training.

For a bright lead against a dark background, the summation of the pixel intensities within the window 908 generates a one-dimensional intensity image represented in graph 916. The side 912 is represented in graph 916 as a rising ramp 918, and the side 914 is represented in graph 916 as a falling ramp 920. The peaks 922 of the first derivative 924 of the graph 916 give the position of the sides 912 and 914. The midpoint of the line connecting the sides 912 and 914 becomes the target bond point, designated "✚" (810). As illustrated, the midpoint does not necessarily fall within the locus 902 defined on the training lead 900.

Although the run-time method uses the midpoint, it should be evident that any point within the locus 902 once aligned with the run-time images is also sufficient. The alignment of the locus can be accomplished using methods known in the art. For instance, the alignment is accomplished by locating the lead bisector 926 of the run-time image directly and recreating the locus 902 or by aligning the locus 902 with the run-time lead 906, where the axis of the aligned locus 902 corresponds to the bisector of the run-time lead 926.

If the window 908 were perfectly aligned with the longitudinal axis 926 of the run-time lead 906, the peaks 922 in the first derivative image 924 would be sharper, and allow a more accurate identification of the position of the edges 912 and 914. However, the offset between the position of the training lead 900 and the position of the run-time lead 906 causes a smearing of the peaks 922 in the first derivative 924.

Figure 10:
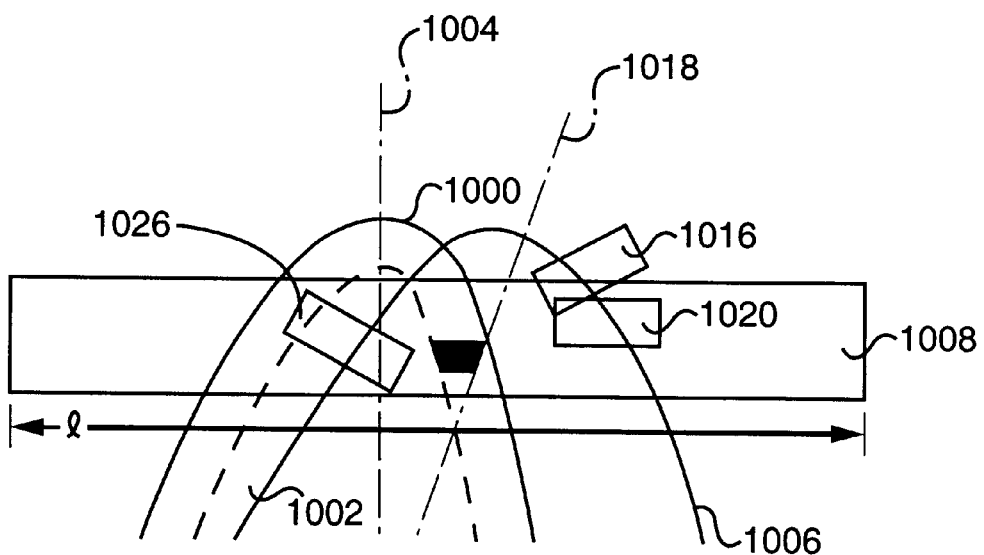
FIGS. 10–10E illustrate part of a non-parallel lead at training and run-time positions, a graph of a one-dimensional intensity image of the width of the lead, and a first derivative of the graph. Also shown are a graph of a one-dimensional intensity image of one side of the lead, and a first derivative of that graph, respectively.

Determining the position of peaks is further exacerbated when the leads are nonparallel as is described with reference to FIGS. 10–10E with continuing reference to FIG. 8. FIG. 10 depicts a position of a nonparallel trained lead 1000, locus 1002, and longitudinal axis of the locus 1004 superimposed over a run-time image of a nonparallel lead 1006 and a search window 1008, not drawn to scale and exaggerated for illustration purposes. Also shown is a graph of a one-dimensional intensity image 1010 and its first derivative 1012 for a bright lead on a dark background, derived as hereinbefore described and exaggerated for illustration purposes. The peaks 1014 are not necessarily symmetric for a non-normal window 1008, and further still are even less sharp than for the displaced lead of FIG. 9. The flatness of the peaks is owing to the smear as previously discussed and the nonparallel nature of the lead sides. When the pixels are summed vertically along the width of the widow 1008, w, the edges comprising the lead side are spread across a number of pixels and produce a more gradual change in the intensity image than would a straight edge somewhat aligned with the width of the window 1008. The flatness of the peaks 1014 makes the identification of the lead edges less certain.

In one embodiment, the positional uncertainty of the edges is improved by searching a plurality of second windows 1016 (806), smaller than the first window 1008. The second windows 1016 are positioned at a plurality of angles and enclose a side of the lead detected by the first window, preferrably starting at the angle of the lead side given during training. One instance of the graph of a one-dimensional intensity image 1022 generated by a second window 1016 is shown in FIG. 10C, and its first derivative1024 is shown in FIG. 10D. The angle of the window 1016 having its width most closely aligned with the lead side will generate the strongest peak in the first derivative from among the plurality of smaller windows 1016, and is designated the maximum angle. The strongest peak is sharper and more easily identified, and, thus, the position of the side more easily identified.

Alternatively, a single smaller window 1020 enclosing part of a side is positioned at the angle of the lead side given during training. The peak of a derivative of an intensity image generated at that angle by window 1020 would also be sharper than 1014 and more easily identified. Thus, the position of the side could be refined.

The second side position can also be refined using the found maximum angle or the training angle. A second small window 1020 is positioned having the training angle or an angle offset substantially equally from the training bisector 1004 or the run-time bisector 1018 as the maximum angle. The second side is searched with a smaller window 1020 at that angle (806). For example, if the lead bisector is at 45°, and the window on the right side that produced the strongest peak was 48° from a plurality of windows, such as 46°, 48°, and 50°, the left side is searched at 43°, which is 3° offset from the bisector.

Figure 10E:
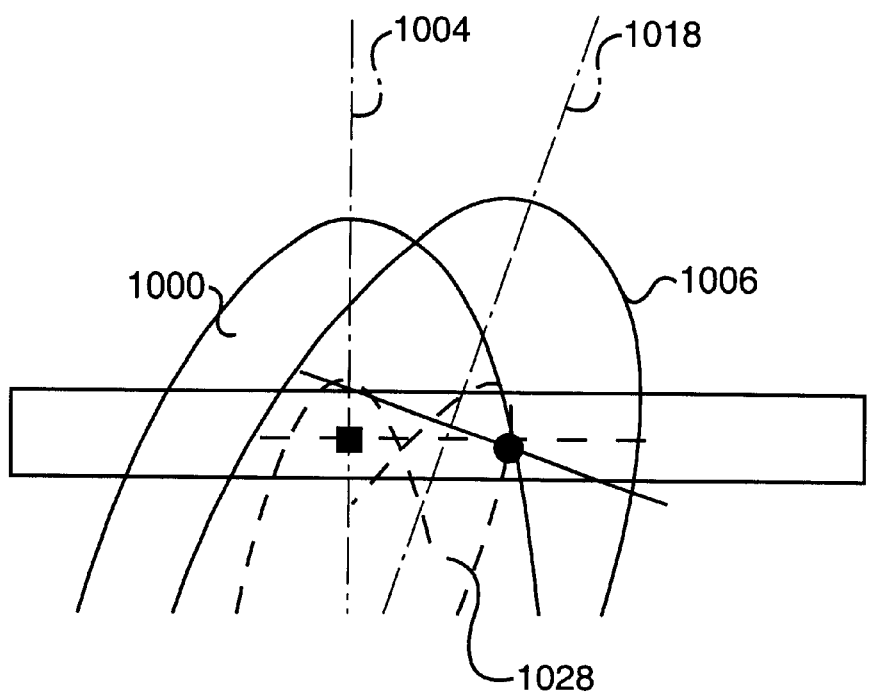
Figure 10A:
Figure 10B:
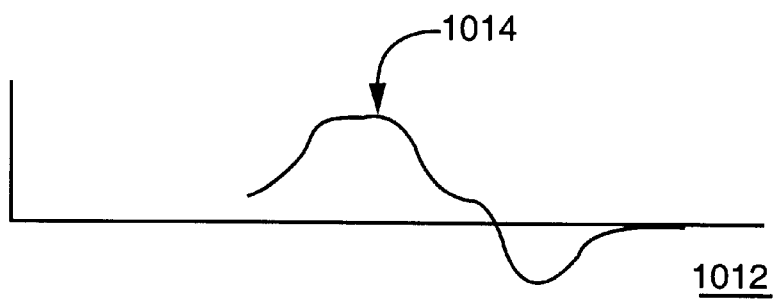
Figure 10C:
Figure 10D:

Additionally, for non-parallel leads, the midpoint is often not on the bisector of the run-time lead 1006 as illustrated in FIG. 10E, not drawn to scale. Where necessary, the target bond point is moved to a position within an aligned locus 1028 and optionally along the bisector of the run-time lead 1018 from "" to . The invention recognizes that this further refinement is usually not necessary, and instead streamlines the run-time procedure.

Preferably, during run-time the distance of the target bond position to the tip is also refined (808).

Further, the length of the window 1008 is optionally refined to maintain the tolerance desired by the user. For instance, if the user tolerance dictates the length of the window 1008 should be three times the lead width, the length of the window 1008 will be enlarged or decreased when the distance to the tip is too large or too small, respectively.

After refinement of the target bond point along the width and optionally along the length of the lead (810) as hereinbefore described, one bond can be formed and the process repeated for each lead, or all positions are found and then bonded (812).

For extremely difficult images, the steps employed during training can be reused during run-time, as shown in FIG. 8B, where like steps are designated by like numerals. The method uses the trained data as input (800), acquires an image of the leads (802), and detects at least a portion of the edges of the lead sides (506) as hereinbefore described. After the lead sides are detected, the locus is defined (508) and the training target bond position is adjusted (510) as was previously described. Thereafter, a bond is formed and the steps repeated for each lead, or all positions are found and then bonded (812).

Figure 11:
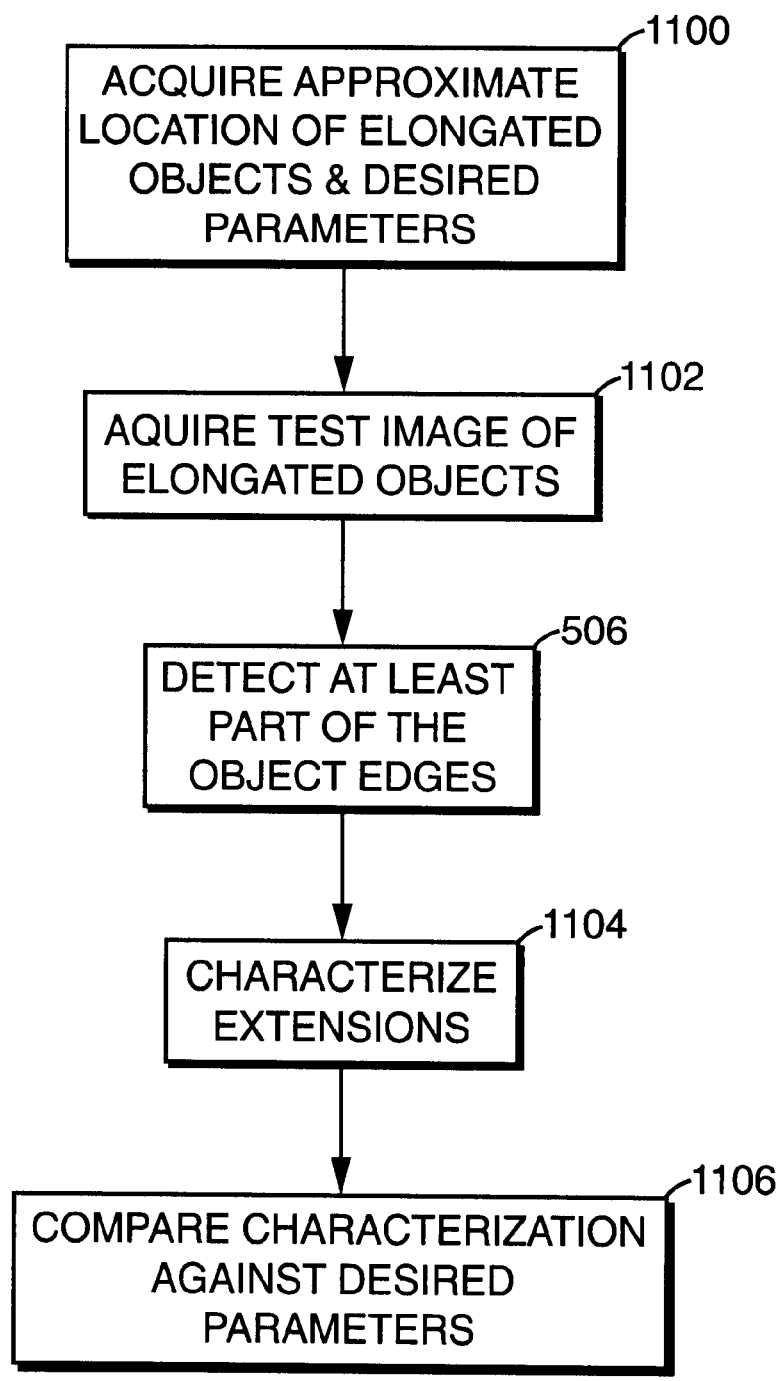
FIG. 11 is a flowchart illustrating another embodiment of the method of the invention.

Turning now to FIG. 11, FIG. 11 shows a flowchart of an inspection embodiment of the method, where steps in the method are denoted in the detailed description in parentheses, and like numerals indicate like steps. The first step is to determine the approximate location of the elongated objects and the desired parameters of the elongated objects (1100), where the parameters can include non-bent leads, converging sides, or the width of the elongated objects at the bond point, for example.

Thereafter, a test image of the elongated objects is acquired (1102), where an image of each elongated object, a plurality of elongated objects, or an object with the plurality of elongated objects can be acquired, as previously described. Thereafter, as previously described, a portion of the edges of the elongated objects are detected (506).

Then, the characteristics of the elongated objects are determined with the techniques previously described (1104), such as bisector angle. It should be apparent that known methods not specifically discussed herein can also be used to characterize the elongated objects, and the characterization does not require both the bisector angle and the target bond point.

The character of the elongated objects in the test image is then compared against the desired parameters (1106). The results of the comparison can be used to accept or reject the object, for a statistical analysis of the quality of the objects, or other reasons known in the art.

Those skilled in the art will realize that the methods and apparatuses of the invention can position point(s), locate point(s), or inspect the point(s) on any elongated object, where an elongated object is an object having a longer longitudinal axis than a normal axis, including objects with a finite normal axis and an infinite longitudinal axis.

Because the definition of the locus can be used for elongated leads of any shape, this method is easily adaptable to use with lead frames having varying shaped leads, such as parallel leads along the lead frame sides and crocked leads at the corners or thick and thin leads, for example.

Those skilled in the art will also realize that using reduced-resolution images to locate the leads, for example, could decrease processing time. Further, any combination of full-resolution and reduced-resolution images can be used. However, use of reduced-resolution images typically results in a loss of accuracy.

Those skilled in the art will realize that processing time can also be decreased by performing any of the computations described herein using sampled data, such as generating lines and characterizing leads, for example. Sampled data is a subset of the available data points, such as every third data point, for instance. It is preferred, however, that reduced-resolution images and sub-sampled data be used in the positioning or precursor steps, such as giving the window position, while the final computations of edges and positions are processed using full-resolution image data.

Those skilled in the art will realize that the elongated objects do not have to be part of one object but can be separate objects.

Those skilled in the art will appreciate that some, or all, of the steps of defining the locus, positioning the target bond point, and characterizing the elongated objects described hereinbefore, can be combined and effected as hardware implementations, software implementations or a combination thereof, and that although one vision system described is implemented with a Cognex vision tools, the invention can be implemented on other platforms, such as general purpose computers running software and/or configured with hardware to effect the functionality described herein.

Furthermore, while an embodiment of operations described herein use a run-time image and a training image, it should be appreciated that any of the images described herein can be subject to further processing, such as by filtering using a gaussian filter, median filter, smoothing filter, morphological filter or the like known in the art, as desired to change image quality.

Other modifications and implementations will occur to those skilled in the art without departing from the spirit and the scope of the invention as claimed. Accordingly, the above description is not intended to limit the invention except as indicated in the following claims.

What is claimed is:

1. A method for defining a region of viable bond points on first elongated objects, the method comprising:
   acquiring data representing the first elongated objects;
   determining at least portions of edges of the first elongated objects using the data;
   defining a locus of viable bond points adapted to receive a bond on the first elongated objects, the locus being a region of the elongated objects having an outer boundary offset from at least a portion of the edges by at least a minimum-offset distance.

2. The method of claim 1, wherein acquiring data includes:
   acquiring an image of the first elongated objects.

3. The method of claim 1, wherein determining at least portions of edges includes:
   determining lines that define at least portions of sides of the first elongated objects.

4. The method of claim 3, wherein defining a locus includes:
   determining a bisector between the lines, and defining a width of the locus as being a predetermined distance from the bisector.

5. The method of claim 4, wherein determining at least portions of edges includes:
   determining a tip of the first elongated objects at an intersection of the bisector and one edge of each of the first elongated objects.

6. The method of claim 5, further comprising:
   positioning a bond point closest to the tip and substantially on the bisector within the locus of viable bond points.

7. The method of claim 4, wherein determining at least portions of edges includes:
   determining a tip of the first elongated objects, the tip being at a position where a line normal to the bisector first touches each of the first elongated objects when moved toward the tip from a position outside each of the first elongated objects.

8. The method of claim 7, further comprising:
   positioning a bond point closest to the tip and substantially on the bisector within the locus of viable bond points.

9. The method of claim 1, wherein determining at least portions of edges includes:
   detecting a tip of the first elongated objects using the data.

10. The method of claim 9, wherein detecting a tip includes:
    detecting the tip independent of the geometry of the sides of each of the elongated objects.

11. The method of claim 1, wherein the locus is an inner region on each of the first elongated objects.

12. The method of claim 1, wherein the elongated objects are leads.

13. The method of claim 1, wherein the elongated objects are part of one object.

14. The method of claim 1, wherein acquiring data includes:
    acquiring separate test images for each of the first elongated objects.

15. The method of claim 1, wherein the minimum-offset distance is equal to at least one-half a dimension of a bond.

16. The method of claim 1, wherein user supplied variables are accommodated, and wherein the minimum-offset distance is a user supplied variable.

17. The method of claim 1, wherein the minimum-offset distance varies along the edges of the first elongated objects.

18. The method of claim 1, wherein determining at least portions of edges of the first elongated objects includes:
    projecting a run-time image within a first window so as to produce a one-dimensional intensity image;
    filtering the one-dimensional intensity image so as to produce a filtered one-dimensional intensity image having enhanced edges within the one-dimensional intensity image corresponding to sides of the first elongated objects; and
    detecting peaks within the filtered one-dimensional intensity image corresponding to edges of the first elongated objects.

19. The method of claim 1, for positioning one or more bond points on second elongated objects, the method further comprising: acquiring a run-time image of the second elongated objects;
    detecting at least a portion of each elongated side of the second elongated objects in the run-time image; and
    positioning one or more bond points on the second elongated objects between at least the portion of each elongated side using the locus of each of the first objects that correspond to each of the second objects in the run-time image.

20. The method of claim 1, for positioning one or more bond points on second elongated objects, wherein the locus has a longitudinal axis and a reference position, the method further comprising:
    acquiring a run-time image of the second elongated objects;
    detecting at least a portion of each elongated side of the second elongated objects in the run-time image by searching a window aligned with the reference position and aligned substantially normal to the longitudinal axis of the locus of each of the first elongated objects that correspond to each of the second elongated objects in the run-time image; and
    positioning one or more bond points on the second elongated objects between at least the portion of each elongated side.

21. The method of claim 20, wherein the first elongated objects are from a model object and the second elongated objects are from a run-time object.

22. The method of claim 20, wherein the sides of at least one of the second elongated objects are not parallel, the method further comprising:
searching a plurality of small windows, each small window smaller than the first window and being positioned at a plurality of angles normal to a portion of one side of the second elongated objects, and being positioned to enclose one side of the second elongated object detected by the window, thereby refining the detection of the side; and
determining one of the plurality of angles as being greatest so as to produce a maximum angle; and
searching a second side of each second elongated object using a single smaller window at an angle from a bisector that is substantially the maximum angle.

23. The method of claim 20, further comprising:
aligning substantially in at least one dimension the first elongated objects with the second elongated objects before detecting at least a portion of each elongated side of the second elongated objects.

24. The method of claim 23, wherein aligning includes:
aligning each of the locus of viable bond points with each of the second elongated objects in the direction normal to the longitudinal angle.

25. The method of claim 20, wherein the reference position corresponds to the target bond position.

26. The method of claim 20, wherein acquiring a run-time image includes:
acquiring separate run-time images for each of the second elongated objects.

27. The method of claim 20, wherein acquiring a run-time image includes:
acquiring multiple fields of view of the run-time image.

28. The method of claim 20, wherein detecting at least a portion of each elongated side of the second elongated objects includes:
detecting lines in the run-time image that define the elongated sides of the second elongated objects.

29. The method of claim 20, wherein positioning one or more bond points includes:
positioning one or more bond points within the locus of viable bond points.

30. The method of claim 20, wherein positioning includes:
aligning substantially in at least one dimension the locus of viable bond points with each of the second elongated objects using the portion of each side of the second elongated objects before positioning.

31. The method of claim 20, wherein the sides of at least one of the first elongated objects are not parallel, and wherein detecting at least a portion of each of the elongated sides includes:
detecting a tip of the second elongated objects using the image; and
varying a search length of the window based on a distance of the reference position from the tip.

32. An apparatus adapted to define one or more bond points on first elongated objects, the apparatus comprising:
test data representing the first elongated objects;
a side detector adapted to determine using the test data at least portions of elongated sides of the first elongated objects using the test data;
a definer, cooperative with the side detector, adapted to define a locus of viable points on each of the first elongated objects as being a region between the sides and offset from the sides by at least a minimum-offset distance, the region being adapted to receive a bond.

33. The apparatus of claim 32, wherein the side detector determines lines that define at least portions of the elongated sides.

34. The apparatus of claim 32, further comprising:
a tip detector, cooperative with the definer, adapted to determine the tip of the first elongated objects using the test data; and
wherein the locus is offset from the lead sides and the lead tip by at least a minimum offset distance.

35. The apparatus of claim 32, adapted to position one or more bond points on second elongated objects, wherein the locus has a longitudinal axis and a reference position, the apparatus further comprising:
a run-time image of the second elongated objects;
the side detector, cooperative with the run-time image and the definer, adapted to detect at least a portion of each side of the second elongated objects in the run-time image by searching a first window aligned at the longitudinal angle and enclosing the reference position of the locus of viable points of the first elongated objects; and
a bond point positioner, cooperative with the run-time image and the side detector, adapted to position the bond point on each second elongated object between the sides.

36. The apparatus of claim 32, adapted to position one or more bond points on second elongated objects, the apparatus further comprising:
a run-time image of the second elongated objects;
the side detector adapted to detect at least a portion of each elongated side of the second elongated objects in the run-time image; and
a bond point positioner, cooperative with the definer and the side detector, adapted to position one or more bond points on the second elongated objects between at least the portion of each elongated side using the locus of each of the first elongated objects that corresponds to each of the second elongated objects in the run-time image.

37. A method for positioning a point on a first elongated object, the method comprising:
acquiring data representing elongated objects;
detecting at least portions of elongated sides of the first elongated objects using the data;
defining a locus of viable points on the elongated objects as being a region between the elongated sides that is offset from the elongated sides by at least a minimum-offset distance.

38. The method of claim 37, further comprising:
detecting a tip of each of the elongated objects; and
wherein defining includes:
defining an inner region having a boundary defined by at least the minimum distance from the elongated sides and the tip.

39. The method of claim 37, wherein detecting at least portions of the sides includes:
determining lines that define at least portions of the sides.

40. An apparatus defining regions on a plurality of first elongated objects, the apparatus comprising:

a test image of the first elongated objects;

first detecting means for detecting lines in the test image that define portions of elongated sides of each of the first elongated objects;

defining means cooperative with the first detecting means for defining a locus of viable points on each of the plurality of first elongated objects as being a region between the sides and offset from the sides by at least a minimum-offset distance.

41. The apparatus of claim 40, adapted to position one or more bond points on second elongated objects, wherein the region has a longitudinal angle and a reference position, the apparatus further comprising:

a run-time image of the second elongated objects;

second detecting means, cooperative with the defining means, for detecting each side of the second elongated objects in the run-time image by searching a first window aligned at the longitudinal angle and enclosing the reference position of the locus of viable points of each of the plurality of the first elongated objects; and positioning means, cooperative with the second detecting means, for positioning the bond point on each of the second elongated object between the edges within the locus of viable points superimposed on the second elongated objects.

* * * * *